United States Patent [19]

Cowley et al.

[11] 3,971,775

[45] July 27, 1976

[54] PROCESS FOR PREPARING PENICILLIN ANTIBIOTICS

[75] Inventors: Brian Richard Cowley, Ruislip; David George Martin, Stoke Poges, both of England

[73] Assignee: Glaxo Laboratories Limited, Greenford, England

[22] Filed: May 2, 1975

[21] Appl. No.: 574,345

[30] Foreign Application Priority Data

May 9, 1974 United Kingdom............... 20584/74

[52] U.S. Cl. ............................................ 260/239.1
[51] Int. Cl.²........................................ C07D 499/68
[58] Field of Search ................................. 260/239.1

[56] References Cited
UNITED STATES PATENTS

3,846,407  11/1974  Huhn et al. ...................... 260/239.1

FOREIGN PATENTS OR APPLICATIONS

| 991,586 | 5/1965 | United Kingdom............... 260/239.1 |
| 1,201,542 | 8/1970 | United Kingdom............... 260/239.1 |
| 1,241,844 | 8/1971 | United Kingdom............... 260/239.1 |
| 1,327,270 | 8/1973 | United Kingdom............... 260/239.1 |

Primary Examiner—Gerald A. Schwartz
Attorney, Agent, or Firm—Bacon & Thomas

[57] ABSTRACT

α-Aminoacylpenicillin antibiotics such as ampicillin and amoxycillin may be prepared in particularly simple manner by a process which comprises preparing a solution of 6-aminopenicillanic acid (6-APA) in a water-immiscible organic solvent by treating 6-APA with an excess of a strong tertiary amine base in the presence of said solvent; neutralising the residual strong tertiary amine base in said solution; reacting the neutralised solution with a solution in a water-immiscible organic solvent of an acylating agent which is a mixed anhydride of a lower alkoxyformic acid and an N-protected derivative of an α-aminoacid wherein the N-protecting group is acid-labile, to yield a solution of an N-protected α-aminoacylpenicillin derivative; contacting the resulting solution with water and a strong acid to cleave the acid-labile N-protecting group; and isolating the thus-obtained α-aminoacylpenicillin from the resulting water-containing system. The use of water-immiscible solvents in the process obviates the need for a solvent evaporation stage during isolation of the α-aminoacylpenicillin product and thus renders the process of particular advantage in plant-scale operations.

10 Claims, No Drawings

PROCESS FOR PREPARING PENICILLIN ANTIBIOTICS

This invention is concerned with the preparation of penicillin compounds, and is particularly concerned with the preparation of α-aminoacylpenicillin antibiotics.

The valuable antibiotic properties of α-aminoacylpenicillins such as ampicillin [i.e. (2′R,3S,5R,6R)-6-(2′-amino-2′-phenylacetamido)-2,2-dimethylpenam-3-carboxylic acid] and amoxycillin [i.e. (2′R,3S,5R,6R)-6-(2′-amino-2′-p-hydroxyphenylacetamido)-2,2-dimethylpenam-3-carboxylic acid] are well known and a number of methods have been proposed for the preparation of compounds of this type. In general such methods involve reaction of 6-aminopenicillanic acid (6-APA) or a derivative thereof, e.g. a salt or a silylated derivative, with an acylating agent which is a reactive derivative of the appropriate α-aminoacid wherein the α-amino group is protected against side reactions by, for example, substitution with an easily removable protecting group, followed by cleavage of this protecting group from the acylated product to yield the desired α-aminoacylpenicillin.

The selection of the reactive derivative of the α-aminoacid to be used as the acylating agent is influenced by factors such as the precise chemical nature of the α-aminoacid. Thus, for example, it is necessary in the synthesis of amoxycillin to select a reactive derivative of D-2-amino-2-p-hydroxyphenylacetic acid in which the reactive grouping is not prone to interference by the hydroxy substituent on the phenyl ring. This requirement precludes, for example, the use of commonly employed reactive derivatives such as acid halides as acylating agents in the synthesis of amoxycillin.

One class of reactive derivatives of α-aminoacids which has attracted interest in the synthesis of α-aminoacylpenicillins, and which may successfully be employed in the synthesis of compounds such as amoxycillin which contain reactive hydroxy groups in the α-aminoacyl side chain, consists of mixed anhydrides formed by reacting an N-protected derivative of the appropriate α-aminoacid in which the N-protecting group is acid-labile with, for exammple, the chloride of an alkyl-substituted acetic acid (e.g. pivalic acid or diethylacetic acid) or with a haloformate ester such as ethyl chloroformate. The use of reactive derivatives of this type as acylating agents is potentially advantageous in that comparatively inexpensive starting materials may be employed, and in some cases these may be recycled. The amine deprotection step is also facilitated by the selection of a protecting group which is cleavable by treatment of the reaction product with aqueous acid.

Acylation using mixed anhydrides derived from an α-aminoacid and a haloformate ester, particularly a lower alkyl haloformate such as ethyl chloroformate, is in principle advantageous on economic grounds, since such anhydrides (hereinafter referred to as "mixed lower alkoxyformic anhydrides", the qualification "lower" being used in this specification to designate groups containing up to 6 carbon atoms) may be prepared substantially more cheaply than alkyl-substituted acetic acid anhydrides. Mixed lower alkoxyformic anhydrides, however, exhibit low stability in the presence of base and this property somewhat complicates their use in the acylation of 6-APA. Thus, whereas the preparation of the mixed anhydride must be carried out under anhydrous conditions to avoid decomposition of the anhydride, it has hitherto generally been thought desirable, in order to optimise the yield of α-aminoacylpenicillin, to employ the 6-APA in an aqueous medium in order to secure maximum dissolution of 6-APA without the need to employ excess base. The use of non-aqueous solvent media for this purpose has generally been avoided since it is necessary to employ excess base (e.g. 2 equivalents) to promote efficient solubilisation of 6-APA in such solvents.

Accordingly, in the majority of previously disclosed processes using mixed lower alkoxyformic anhydride acylating agents, the anhydride formation reaction is carried out in an anhydrous, water-miscible organic solvent such as acetone or tetrahydrofuran, an aqueous or partially aqueous solution of a salt of 6-APA subsequently being added to the thus-obtained anhydride solution. In this method it is necessary to remove the water-miscible organic solvent by evaporation, either before or after removal of the amine protecting group, as a preliminary step in the isolation of the α-aminoacylpenicillin product, and this need for a solvent evaporation stage in the work-up of the product is a considerable disadvantage in large scale applications of the process in view of the plant requirements and operating costs which it necessarily involves.

We have now found, however, that it is possible successfully to acylate 6-APA with a mixed lower alkoxyformic anhydride under non-aqueous conditions in a water immiscible organic solvent, whereby the desired α-aminoacylpenicillin product may be isolated in a particularly simple manner without the need for a solvent evaporation stage. In addition to the economic benefits which result from the avoidance of a solvent evaporation stage, we have found that it is possible using such anhydrous reaction conditions to achieve higher yields of α-aminoacylpenicillins than have hitherto been shown in connection with the reaction of 6-APA and mixed lower alkoxyformic anhydride acylating agents under aqueous conditions. Accordingly the non-aqueous reaction procedure herein described possesses substantial economic and practical advantages over previously disclosed mixed lower alkoxyformic anhydride routes to α-aminoacylpenicillin antibiotics and is particularly suited to the plant-scale preparation of such antibiotics.

The process of the present invention is based on our discovery that a solution of an organic base salt of 6-APA in a non-aqueous, water-immiscible solvent, obtained by treating 6-APA with an excess of a strong tertiary amine base in the presence of the said solvent, may be acylated in good yield by treatment with a mixed lower alkoxyformic anhydride provided that the residual strong base in the solution is neutralised prior to addition of the said mixed anhydride.

The invention may thus be regarded as a process for the preparation of an α-aminoacylpenicillin antibiotic which comprises (i) contacting 6-APA with an excess of a strong tertiary amine base in the presence of a water-immiscible inert organic solvent to yield a solution of a salt of 6-APA with said base in said solvent; (ii) neutralising the residual strong tertiary amine base in said solution; (iii) contacting the resulting neutralised solution with a solution in a water-immiscible inert organic solvent of a mixed anhydride of a lower alkoxyformic acid and an N-protected derivative of an α- aminoacid wherein the N-protecting group is acid-labile, to yield a solution of an N-protected α-aminoacylpenicillin derivative; (iv) contacting the resulting solution with water and a strong acid to cleave the acid-labile N-protecting group; and (v) isolating the thus-obtained α-aminoacylpenicillin antibiotic from the resulting water-containing system.

The process of the invention is of especial value in the preparation of penicillin compounds wherein the α-aminoacyl side chain is a 2-amino-2-phenylacetyl group or such a group wherein the phenyl moiety carries one or more substituents, and for convenience the process is hereinafter described with particular reference to the preparation of compounds of this type. It should be appreciated, however, that the process is not in any way limited to the preparation of such α-amino(phenylacetyl) penicillin compounds.

The invention will now be described in detail with respect to each of the five component steps of the process.

i. PREPARATION OF A WATER-IMMISCIBLE SOLUTION OF 6-APA.

The strong tertiary amine base employed in this step should have a pKa of at least 9, preferably at least 10. Suitable bases thus include tri(lower alkyl)amines such as trimethylamine, triethylamine and tri-n-butylamine, the use of triethylamine being preferred. Water-immiscible solvents which may be used include chlorinated hydrocarbons such as methylene chloride and chloroform. Both the base and the solvent should be substantially water-free.

Dissolution of the 6-APA is conveniently effected by stirring or otherwise agitating a suspension of 6-APA in the chosen solvent, in which 1.5–3, preferably about 2, equivalents of the base have been dissolved. This step may be carried out at a temperature in the range of from 10°C up to the reflux temperature of the system, but since dissolution of 6-APA proceeds at a satisfactory rate at ambient temperature, normally being complete within 1–3 hours at about 25°C, we prefer to conduct the dissolution step without the application of external heating.

ii. NEUTRALISATION OF THE RESIDUAL STRONG BASE.

The neutralisation step should similarly be conducted under anhydrous conditions and will require the addition of $(x - 1)$ equivalents of acid where $x$ is the number of equivalents of strong base used to dissolve the 6-APA in step (i). If desired, a slight excess of acid, e.g. up to 0.02 equivalents, conveniently about 0.0125 equivalents, may be added in addition to the required $(x-1)$ equivalents.

Neutralisation is advantageously effected by addition of an appropriate amount of a salt of a weak base with a strong acid, such salts effectively comprising an easily measurable source of strong acid in anhydrous form. The weak base should have a pKa of less than 7, preferably less than 3, suitable bases thus including N,N-disubstituted amides such as N,N-dimethylformamide and N,N-dimethylacetamide. The strong acid may be a mineral acid such as hydrochloric acid or hydrobromic acid, or a strong organic acid such as trifluoroacetic acid or p-toluene sulphonic acid; mineral acids are preferred by virtue of their lower cost. An example of a preferred weak base - strong acid salt for use in this step is N,N-dimethylacetamide hydrochloride.

Other methods of neutralisation which may be employed include the addition of a measured amount of a standardised solution of an acid such as hydrogen chloride in an anhydrous water-immiscible solvent, conveniently the same solvent as is employed for step (i).

The temperature employed for the neutralisation is not critical, and the reaction may conveniently be conducted at ambient temperature. Alternatively the reaction system may be cooled, e.g. to 0°C.

iii. REACTION OF THE 6-APA SALT WITH THE MIXED ANHYDRIDE a. Preparation of the mixed anhydride.

Mixed lower alkoxyformic anhydrides which may be used in the present process include compounds represented by the general formula

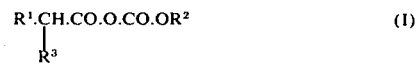

(I)

wherein $R^1$ represents phenyl or phenyl substituted by, for example, one or more of halo (e.g. chloro or bromo), hydroxy, lower (i.e. $C_{1-6}$) alkyl (e.g. methyl), nitro, lower alkylamino (e.g. methylamino), di(lower alkyl) amino (e.g. dimethylamino), lower alkanoyl (e.g. acetyl), lower alkanoylamido (e.g. acetamido), lower alkoxy (e.g. methoxy or ethoxy), and lower alkylthio (e.g. methylthio); $R^2$ represents lower alkyl (e.g. methyl or ethyl); and $R^3$ represents a protected amino group wherein the protecting group is acid-labile.

The nature of the protecting group in $R^3$ is not critical and in general any of the acid-labile amine protecting groups described in the literature may be used. Suitable protecting groups thus include lower alkoxycarbonyl groups such as t-butoxycarbonyl; aralkoxycarbonyl groups such as p-methoxy-benzloxycarbonyl and diphenylmethoxycarbonyl; cycloalkoxycarbonyl groups such as adamant-1-yloxycarbonyl; aralkyl groups such as trityl; and arylsulphenyl groups such as o- or p-nitrophenylsulphenyl. The amino group may also be protected as an imino group by reaction with a carbonyl compound, particularly an o-hydroxy aromatic aldehyde such as salicylaldehyde, 5-chlorosalicylaldehyde, 3,5-dichlorosalicylaldehyde, 2-hydroxy-1-naphthaldehyde or 3-hydroxypyridine-4-aldehyde.

We prefer, however, to employ mixed lower alkoxyformic anhydrides in which the amino group is protected as an enamine grouping. Such protecting groups may be introduced by reaction of the α-aminoacid, preferably in the form of a salt (e.g. an alkali metal salt such as the sodium salt), with a β-dicarbonyl compound, for example a compound of general formula

(II)

[where $R^4$ and $R^5$ are each selected from hydrogen, lower alkyl (e.g. methyl, ethyl, n-propyl or isopropyl), aryl lower alkyl (e.g. benzyl or phenethyl) and aryl (e.g. phenyl), and $R^6$ represents an atom or group as defined for $R^4$ and $R^5$ or a lower alkoxy (e.g. methoxy or ethoxy), aryl lower alkoxy (e.g. benzyloxy) or aryloxy (e.g. phenoxy) group or a group -$NR^7R^8$ (where $R^7$ and $R^8$ are each selected from hydrogen, lower alkyl and aryl or together with the attached nitrogen atom form a heterocyclic ring such as piperidino or morpholino); or two of $R^4$, $R^5$ and $R^6$ together with the interconnecting carbon atoms form a $C_{5-7}$ cycloaliphatic group or $R^5$ and $R^4$ or $R^6$ together with the interconnecting carbon atoms form an aryl group such as phenyl or naphthyl (the compound then existing as the appropriate enol tautomer of the molecule represented by formula II), the remaining group $R^4$, $R^5$ or $R^6$ being as defined above] to yield an enamine protected $\alpha$-aminoacid derivative, for example a compound of formula

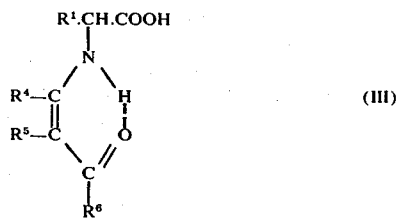

(III)

(where $R^1$, $R^4$, $R^5$ and $R^6$ have the above-defined meanings) or a salt thereof. Examples of $\beta$-dicarbonyl compounds which may be employed in the preparation of enamine protected $\alpha$-aminoacid derivatives include acetylacetone, propionylacetone, butyrylacetone, isobutyrylacetone, benzoylacetone, formylacetone (e.g. in the form of an alkali metal salt), methyl acetoacetate, ethyl acetoacetate, acetyl acetophenone, $\alpha$-acetyl-propiophenone, $\alpha$-benzoylpropiophenone, 3-methyl-2,4-diketopentane, 3-phenyl-2,4-diketopentane, 3,5-diketo-2,6-dimethylheptane, 3-($\beta$-phenethyl)-2,4-diketopentane, N,N-dimethylacetoacetamide, morpholinocarbonylacetone and piperidinocarbonylacetone. A preferred enamine-type protecting group for use in the present process is the 1-methoxycarbonylpropen-2-yl group, obtained by reaction of the $\alpha$-aminoacid or a salt thereof with methyl acetoacetate.

Mixed lower alkoxyformic anhydrides of formula I are conveniently prepared by reacting a salt (e.g. an alkali metal salt such as the sodium salt) of an N-protected $\alpha$-aminoacid having the formula

(IV)

(where $R^1$ and $R^3$ have the above-defined meanings) with a lower alkyl haloformate (e.g. a chloroformate such as ethyl chloroformate) in a suitable water-immiscible inert organic solvent. The reaction is base-catalysed and is preferably carried out in the presence of a tertiary amine such as N-methylmorpholine or N,N-dimethylbenzylamine.

The water-immiscible solvent used in the reaction should be sufficiently polar to solubilise the reactants to an extent which permits their efficient interaction at a temperature low enough to avoid substantial thermal decomposition of the mixed anhydride product. A suitable solvent for this purpose is methyl isobutyl ketone (4-methylpentan-2-one); using this solvent a satisfactory anhydride formation reaction may be achieved at temperatures in the range $-15°$ to $+10°C$, a preferred temperature range being $-10°$ to $0°C$.

The anhydride formation is conveniently effected by adding the N-protected $\alpha$-aminoacid or a salt thereof to a solution of the lower alkyl haloformate and basic catalyst in the chosen solvent, e.g. with stirring. The haloformate is advantageously used in slight excess (e.g. in an excess of up to 0.05 moles), and it is convenient to employ about 0.01 equivalents of the basic catalyst. Reaction times of about one hour will generally be sufficient when using these conditions and the preferred reaction temperatures disclosed above.

b. Reaction of the Mixed Anhydride

The order of addition of the mixed lower alkoxyformic anhydride and neutralised 6-APA salt solutions is not unduly critical, but in practice it is convenient to add the 6-APA solution to the mixed lower alkoxyformic anhydride solution. The acylation may be carried out at a temperature in the range $-50°$ to $+30°C$, preferably $-30°$ to $0°C$, reaction times typically being about 30–90 minutes.

iv. ACID-INDUCED CLEAVAGE OF THE AMINE PROTECTING GROUP

As indicated above, the amine protecting group is cleaved by addition of water and a strong acid to the water-immiscible solution of the N-protected $\alpha$-aminoacylpenicillin derivative obtained from step (iii). The cleavage reaction may be conducted in the cold, i.e. at ambient temperature or with cooling, e.g. to 0°C, for example by adding about a quarter volume of water and then adding a strong acid until the pH of the aqueous phase of the resulting two phase mixture is about 1–2. Alternatively the strong acid may be added in portions at a rate such that the pH remains as high as is compatible with the liberated $\alpha$-aminoacylpenicilllin remaining in solution as an acid addition salt; conveniently a pH of just below about 3.5 is maintained for this purpose.

Strong acids useful in this step of the process include mineral acids such as hydrochloric acid and strong organic acids such as toluene-p-sulphonic acid. The use of toluene-p-sulphonic acid is particularly convenient where ampicillin is being prepared since it induces precipitation of ampicillin toluene-p-sulphonate and thus facilitates isolation of the product.

In general cleavage of the amine protecting group will be substantially complete within 30–90 minutes.

v. ISOLATION OF THE $\alpha$-AMINOACYLPENICILLIN

A convenient method of isolation comprises the addition of base, e.g. a strong inorganic base such as sodium hydroxide, either to the two phase reaction mixture obtained from the cleavage step or to the aqueous phase thereof after separation from the reaction mixture, in order to precipitate the $\alpha$-aminoacylpenicillin product. The pH of the solution is advantageously raised to the isoelectric point of the $\alpha$-aminoacylpenicillin, e.g. to pH 5.2 in the case of amoxycillin, to induce the precipitation.

As indicated above, the $\alpha$-aminoacylpenicillin antibiotic may in certain instances be isolated directly from the N-protecting group cleavage step by using in that step an acid which forms a substantially insoluble salt with the penicillin. Thus, for example, ampicillin may be precipitated directly as its toluene-p-sulphonate salt.

The following non-limitative examples serve to illustrate the invention. All temperatures are in °C.

A. Preparation of (2'R,3S,5R,6R)-6-[2'-amino-2'-(p-hydroxyphenyl)acetamido]-2,2-dimethylpenam-3-carboxylic acid trihydrate (amoxycillin trihydrate)

Example 1

A suspension of (3S,5R,6R)-6-amino-2,2-dimethylpenam-3-carboxylic acid (6-APA - 4.326 g, 0.02 mole) in dried methylene chloride (130 ml) containing triethylamine (5.6 ml, 0.04 mole) was stirred at ca. 25° until solution had been obtained (ca. 1 hour). This solution was cooled to 0°, treated with N,N-dimethylacetamide hydrochloride (2.50 g, 0.02025 mole) and stirred and cooled to −10°.

Meanwhile, 4-methylpentan-2-one (130 ml) was stirred and cooled to 0° and ethyl chloroformate (2.0 ml, 0.0208 mole) and a 1% solution of N-methylmorpholine in 4-methylpentan-2-one (3ml) were added. The solution was cooled to −10° and sodium (R)-N-(1-methoxycarbonylpropen-2-yl)-α-amino-p-hydroxyphenylacetate (5.87 g, 0.02 mole) was added. The suspension was stirred at −10° for 30 minutes, cooled to −20° and then added to the solution of 6-amino-2,2-dimethylpenam-3-carboxylic acid prepared above. The mixture was stirred at 0° for 40 minutes when water (50 ml) was added. The stirred two-phase mixture was acidified to pH 1 with concentrated hydrochloric acid; a solid precipitated which went into solution on stirring at 0° to 5° for 35 minutes. The aqueous phase was adjusted to pH 5.2 with 10% potassium hydroxide solution, and the white suspension was stirred and cooled to 0° for 1 hour and filtered. The filter was washed with ice-cold water (20 ml) and ethyl acetate (20 ml), and the solid was air dried at 35° to give (2'R,3S,5R,6R)-6-[2'-amino-2'-(p-hydroxyphenyl)acetamido]-2,2-dimethylpenam-3-carboxylic acid trihydrate (5.88 g, 70% th.), $[\alpha]_D^{25} + 241°$ (c 0.9; 0.1 N HCl) with infrared and proton magnetic resonance spectra identical to an authentic sample of amoxycillin trihydrate.

Example 2

A suspension of 6-APA (4.326 g, 0.02 mole) in dried methylene chloride (130 ml) containing triethylamine (5.6 ml, 0.04 mole) was stirred at ca. 25° until solution had been obtained (ca. 1 hour). This solution was cooled to 0°, treated with N,N-dimethylacetamide hydrochloride (2.50 g, 0.02025 mole) and stirred and cooled to −10°.

Meanwhile, 4-methylpentan-2-one (70 ml) was stirred and cooled to 0° and ethyl chloroformate (2.0 ml, 0.0208 mole) and a 1% solution of N-methylmorpholine in 4-methylpentan-2-one (3 ml) was added. The solution was cooled to −5° and sodium (R)-N-(1-methoxycarbonyl propen-2-yl)-α-amino-p-hydroxyphenylacetate (5.87 g, 0.02 mole) was added. The suspension was stirred at 0° to −5° for 30 minutes, cooled to −30° and then added to the solution of 6-APA prepared above. The mixture was stirred at −30° for 45 minutes when water (50 ml) was added. The stirred two-phase mixture was acidified to pH 1.1 with concentrated hydrochloric acid and stirred at 0° to 2° for 75 minutes, during which time a white precipitate separated. The mixture was adjusted to pH 5.2 with 10% aqueous potassium hydroxide solution, and the white suspension was stirred and cooled to 0° for 1 hour and filtered. The filter was washed with ice-cold water (20 ml) and ethyl acetate (20 ml), and the solid was air dried at 35° to give amoxycillin trihydrate (6.33 g, 75.5% th.), $[\alpha]_D^{25} + 237°$ (c 0.9; 0.1 N HCl).

Example 3

The procedure of Example 2 was repeated with the mixed anhydride and 6-APA solution both cooled to −2° before mixing, and the acylation was allowed to proceed for 45 minutes at −20°. No solid was present at the end of the acid hydrolysis so the aqueous phase was separated and adjusted to pH 5.2 to give amoxycillin trihydrate (5.96 g, 71.1% th.), $[\alpha]_D + 239°$ (c 1.15; 0.1 N HCl).

Example 4

The procedure of Example 2 was repeated with the mixed anhydride and 6-APA solutions both cooled to −40° before mixing, and the acylation was allowed to proceed for 90 minutes at −40°. Isolation as in Example 3 gave amoxycillin trihydrate (5.67 g, 67.7% th).

Example 5

The procedure of Example 2 was repeated but the 6-APA solution was added to the mixed anhydride solution. Isolation as in Example 3 gave amoxycillin trihydrate (6.60 g, 78.7% th.), $[\alpha]_D^{25} + 237°$ (c 1.1; 0.1 N HCl).

Example 6

The procedure of Example 2 was repeated with the dried methylene chloride being replaced by chloroform (130 ml), to give amoxycillin trihydrate (6.14 g, 73.2% th), $[\alpha]_D^{25} + 237.5°$ (c 1.00; 0.1 N HCl).

B. Preparation of (2'R,3S,5R,6R)-6-(2'-amino-2'-phenylacetamido)-2,2-dimethylpenam-3-carboxylic acid toluene-p-sulphonate (ampicillin toluene-p-sulphonate)

Example 7

A suspension of 6-APA (4.326 g, 0.02 mole) in dried methylene chloride (130 ml) containing triethylamine (5.6 ml, 0.04 mole) was stirred at ca. 25° for 75 minutes, when a clear solution had been obtained. This solution was cooled to 0°, treated with N,N-dimethylacetamide hydrochloride (2.50 g, 0.02025 mole) and stirred and cooled to −30°.

Meanwhile, 4-methylpentan-2-one (70 ml) was stirred and cooled to 0° and ethyl chloroformate (2.0 ml, 0.0208 mole) and a 1% solution of N-methylmorpholine in 4-methylpentan-2-one (3 ml) were added. The solution was cooled to −5° and sodium (R)-N-(1-methoxycarbonylpropen-2-yl)-α-aminophenylacetate (5.42 g, 0.02 mole) was added. The suspension was stirred at 0° to −5° for 30 minutes and then cooled to −30°. The 6-APA solution prepared above was added so as to keep the temperature of the mixture between −25 and −30°. The mixture was stirred for 30 minutes at −30° when water (50 ml) was added. Aqueous 2.53 M toluene-p-sulphonic acid monohydrate solution (17 ml, 0.043 mole) together with 10 M aqueous sodium hydroxide solution (ca. 0.1 ml) were added to the stirred two-phase mixture to adjust the pH to and maintain it at 1.5. The mixture was stirred at 5° for 1 hour when more toluene-p-sulphonic acid solution was added to readjust the pH from 2.5 to 1.6. The resulting suspension was stirred for a further 2 hours at 5° and filtered. The wet cake was washed with 4-methylpentan-2-one (50 ml), sucked as dry as possible and washed by slurrying with ice-cold water (50 ml). The solid was refiltered, washed with ethyl acetate (20 ml) and dried in vacuo at 45° to give ampicillin toluene-p-sulphonate (8.51 g, 81.7% th.), $[\alpha]_D^{25} + 173°$ (c 0.97; 0.2 M pH 7 phosphate buffer).

We claim:

1. In a process for the preparation of an α-aminoacylpenicillin antibiotic of formula

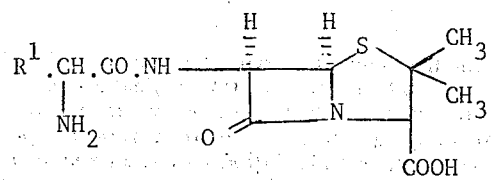

wherein $R^1$ represents phenyl or phenyl substituted by chloro, bromo, hydroxy, lower alkyl, nitro, lower alkylamino, di(lower alkyl)amino, lower alkanoyl, lower alkanoylamido, lower alkoxy or lower alkylthio, by acylating 6-aminopenicillanic acid with a mixed anhydride of formula

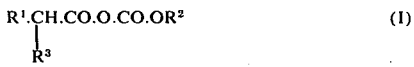

wherein $R^1$ is as defined above, $R^2$ represents lower alkyl and $R^3$ represents a protected amino group wherein the protecting group is acid labile, and thereafter cleaving the acid-labile amine protecting group from the resulting N-protected α-aminoacylpenicillin derivative, the improvement whereby there is obviated the need for a solvent evaporation stage during isolation of an α-aminoacylpenicillin product, which improvement consists of the steps (i) contacting the 6-amino penicillanic acid with about 1.5-3 moles of a tri(lower alkyl)amine in the presence of a solvent selected from the group consisting of methylene chloride and chloroform at a temperature of from about 10°C to the reflux temperature of the solvent to yield a solution of a tri(lower alkyl)amine salt of 6-aminopenicillanic acid in said solvent; (ii) adding an anhydrous acid to the 6-aminopenicillanic acid salt solution to neutralise the residual tri(lower alkyl)amine therein; (iii) contacting the resulting neutralised solution with a solution of the mixed anhydride in methyl isobutyl ketone at a temperature of from about −50°C to about +30°C to yield a solution of the N-protected α-aminoacylpenicillin derivative; (iv) contacting said solution with water and a strong acid selected from the group consisting of mineral acids and toluene-p-sulphonic acid to cleave the acid-labile amine protecting group; and (v) recovering the α-aminoacylpenicillin or an acid addition salt thereof from the resulting water-containing system.

2. The process of claim 1 wherein about 2 moles of the tri(lower alkyl)amine are employed to promote solution of the 6-aminopenicillanic acid.

3. The process of claim 1 wherein the anhydrous acid used to neutralise residual tri(lower alkyl)amine is a salt of a weak base having a pKa of less than 7 and a mineral acid.

4. The process of claim 1 wherein an excess of acid of up to 0.02 equivalent is added during neutralisation of the residual tri(lower alkyl)amine.

5. The process of claim 1 wherein the N-protected amino group $R^3$ in the mixed anhydride of formula I is an enamine group of formula

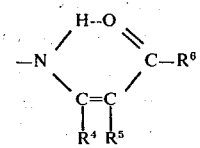

where $R^4$ and $R^5$ are each hydrogen, lower alkyl, phenyl lower alkyl or phenyl; $R^6$ is hydrogen, lower alkyl, phenyl lower alkyl, phenyl, lower alkoxy, phenyl lower alkoxy, phenoxy, piperidino, morpholino or the group —$NR^7R^8$ where $R^7$ and $R^8$ are each hydrogen, lower alkyl or phenyl; or two of $R^4$, $R^5$ and $R^6$ together with the interconnecting carbon atoms form a $C_{5-7}$ cycloalkyl group or $R^5$ together with $R^4$ or $R^6$ forms a phenyl or naphthyl group, the remaining group $R^4$, $R^5$ and $R^6$ being as defined above.

6. The process of claim 1 wherein the amine protecting group in the protected amino group $R^3$ in the mixed anhydride of formula I is 1-methoxycarbonylpropen-2-yl.

7. The process of claim 1 wherein the solution of the N-protected α-aminoacylpenicillin derivative is treated with water and the strong acid to give a two phase mixture in which the aqueous phase has a pH in the range 1–2, and base is added to the resulting water-containing system or to the aqueous phase after separation from the organic solvent system to adjust the pH of the aqueous solution to the isoelectric point of the α-aminoacylpenicillin and thereby precipitate said α-aminoacylpenicillin.

8. The process of claim 1 wherein a mixed anhydride of formula I in which $R^1$ is phenyl is employed and toluene-p-sulphonic acid is added to the solution of the N-protected α-aminoacylpenicillin derivative to cleave the amine protecting group and precipitate ampicillin toluene-p-sulphonate.

9. A process for the preparation of ampicillin toluene-p-sulphonate which consists of the steps (i) contacting 6-aminopenicillanic acid with about 2 moles of triethylamine in the presence of a solvent selected from the group consisting of methylene chloride and chloroform at a temperature of from about 10°C to the reflux temperature of the solvent to yield a solution of the triethylammonium salt of 6-aminopenicillanic acid in said solvent; (ii) adding N,N-dimethylacetamide hydrochloride to said solution to neutralise the residual triethylamine; (iii) contacting the neutralised solution with a solution of a mixed anhydride of formula

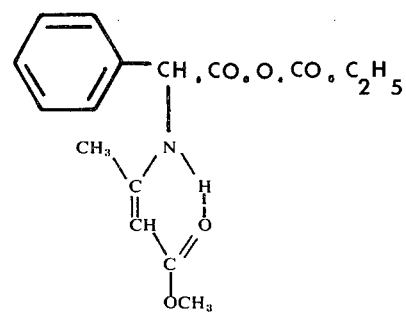

in methyl isobutyl ketone at a temperature of from about −50°C to about + 30°C to yield a solution of an N-protected ampicillin derivative in which the N-protecting group is 1-methoxycarbonylpropen-2-yl; and (iv) contacting said solution with water and toluene-p-sulphonic acid to cleave the N-protecting group and precipitate ampicillin toluene-p-sulphonate whereby there is obviated the need for a solvent evaporation stage during isolation of the ampicillin toluene-p-sulfonate product.

10. A process for the preparation pf amoxycillin which consists of the steps (i) contacting 6-aminopenicillanic acid with about 2 moles of triethylamine in the presence of a solvent selected from the group consisting of methylene chloride and chloroform at a temperature of from about 10°C to the reflux temperature of the solvent to yield a solution of the triethylammonium salt of 6-aminopenicillanic acid in said solvent; (ii) adding N,N-dimethylacetamide hydrochloride to said solution to neutralise the residual triethylamine; (iii) contacting the neutralised solution with a solution of a mixed anhydride of formula

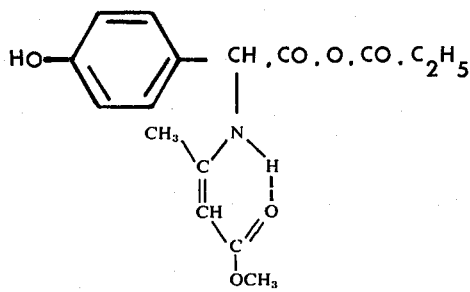

in methyl isobutyl ketone at a temperature of from about −50°C to about + 30°C to yield a solution of an N-protected amoxycillin derivative in which the N-protecting group is 1-methoxycarbonylpropen-2-yl; (iv) contacting said solution with water and hydrochloric acid to cleave the N-protecting group; and (v) adding sodium hydroxide or potassium hydroxide to the resulting water-containing system or to the aqueous phase after separation from the organic solvent system to adjust the pH of the aqueous system to 5.2 and thereby precipitate amoxycillin whereby there is obviated the need for a solvent evaporation stage during isolation of the amoxycillin product.

* * * * *